US010705101B2

(12) United States Patent
Kleinfeld et al.

(10) Patent No.: US 10,705,101 B2
(45) Date of Patent: Jul. 7, 2020

(54) DETERMINATION OF THE UNBOUND FREE FATTY ACID PROFILES IN BIOLOGICAL AND INDUSTRIAL SPECIMENS

(71) Applicant: Alan Kleinfeld, La Jolla, CA (US)

(72) Inventors: Alan Kleinfeld, La Jolla, CA (US); Andrew Huber, Encinitas, CA (US)

(73) Assignee: Alan Kleinfeld, La Jolla, CA (US)

( * ) Notice: Subject to any disclaimer, the term of this patent is extended or adjusted under 35 U.S.C. 154(b) by 299 days.

(21) Appl. No.: 15/037,910

(22) PCT Filed: Dec. 2, 2014

(86) PCT No.: PCT/US2014/068240
§ 371 (c)(1),
(2) Date: May 19, 2016

(87) PCT Pub. No.: WO2015/084894
PCT Pub. Date: Jun. 11, 2015

(65) Prior Publication Data
US 2016/0282368 A1    Sep. 29, 2016

Related U.S. Application Data

(60) Provisional application No. 61/911,409, filed on Dec. 3, 2013, provisional application No. 61/947,865, filed on Mar. 4, 2014.

(51) Int. Cl.
*G01N 33/92* (2006.01)
*G01N 33/58* (2006.01)

(52) U.S. Cl.
CPC .......... *G01N 33/92* (2013.01); *G01N 33/582* (2013.01); *G01N 2500/10* (2013.01); *G01N 2800/085* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| 5,470,714 | A | 11/1995 | Kleinfeld |
|---|---|---|---|
| 6,444,432 | B1 | 9/2002 | Kleinfeld |
| 6,750,030 | B2 | 6/2004 | Kleinfeld |
| 6,999,173 | B2 | 2/2006 | Kleinfeld et al. |
| 7,202,089 | B2 | 4/2007 | Kleinfeld |
| 7,262,017 | B2 | 8/2007 | Kleinfeld |
| 7,601,510 | B2 | 10/2009 | Kleinfeld et al. |
| 7,879,558 | B2 | 2/2011 | Kleinfeld |
| 8,466,090 | B2 | 6/2013 | Kleinfeld et al. |
| 9,134,317 | B2 | 9/2015 | Kleinfeld et al. |
| 9,164,109 | B2 | 10/2015 | Kleinfeld et al. |
| 2006/0257938 | A1 | 11/2006 | Kleinfeld et al. |
| 2015/0044692 | A1 | 2/2015 | Kleinfeld et al. |

OTHER PUBLICATIONS

Kleinfeld (SBIR STTR, Profiling Plasma Unbound Free Fatty Acids for Early Dectection of Stroke, 2010, 3 pages).*
Extended European Search Report for European Patent Application No. 14866898.1, dated May 26, 2017.
Bhardwaj et al., "A multicenter comparison of established and emerging cardiac biomarkers for the diagnostic evaluation of chest pain in the emergency department," *American Heart Journal*, vol. 162(2), pp. 276-282.e1 (May 27, 2011).
Huber et al., "Fatty Acid-Specific Fluorescent Probes and Their Use in Resolving Mixtures of Unbound Free Fatty Acids in Equilibrium with Albumin," *Biochemistry*, vol. 45(48), pp. 14263-14274 (2006).
Spector, "Part III. Lipids, hormones, and atherogenes. The transport and utilization of free fatty acid," *Annals of the New York Academy of Sciences*, vol. 149, pp. 768-783 (1968).

* cited by examiner

*Primary Examiner* — G Steven Vanni
(74) *Attorney, Agent, or Firm* — Knobbe, Martens, Olson & Bear LLP

(57) ABSTRACT

The invention relates to determination of the profile of unbound free fatty acids (FFAu) in biological samples, such as human and animal blood specimens and plant and animal oils, by measuring the fluorescence response of sets of different fluorescently labeled fatty acid binding proteins (probes) that undergo a change in fluorescence ratio at 2 wavelengths upon binding an FFAu. Use of these profiles in human and animal disease, in basic research, in drug development and in industrial uses is disclosed.

19 Claims, 6 Drawing Sheets

Specification includes a Sequence Listing.

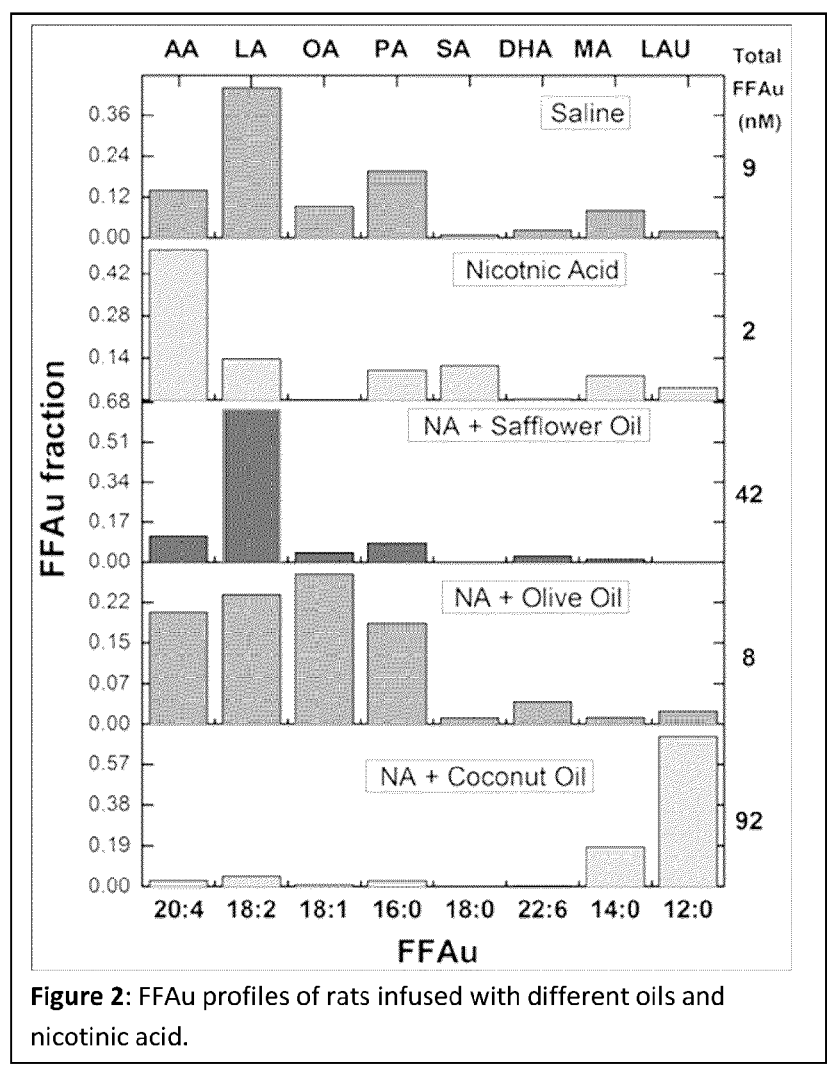
Figure 2: FFAu profiles of rats infused with different oils and nicotinic acid.

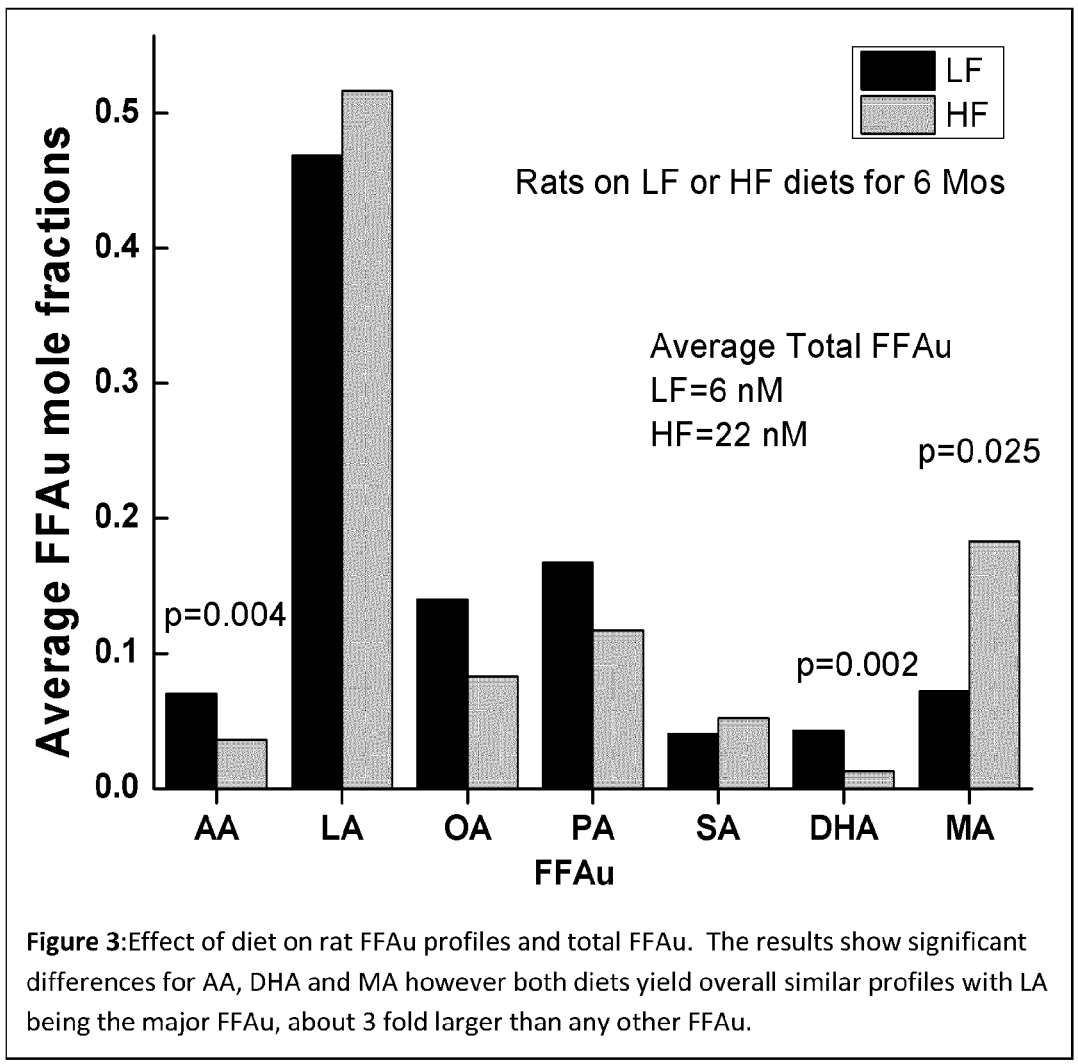
Figure 3: Effect of diet on rat FFAu profiles and total FFAu. The results show significant differences for AA, DHA and MA however both diets yield overall similar profiles with LA being the major FFAu, about 3 fold larger than any other FFAu.

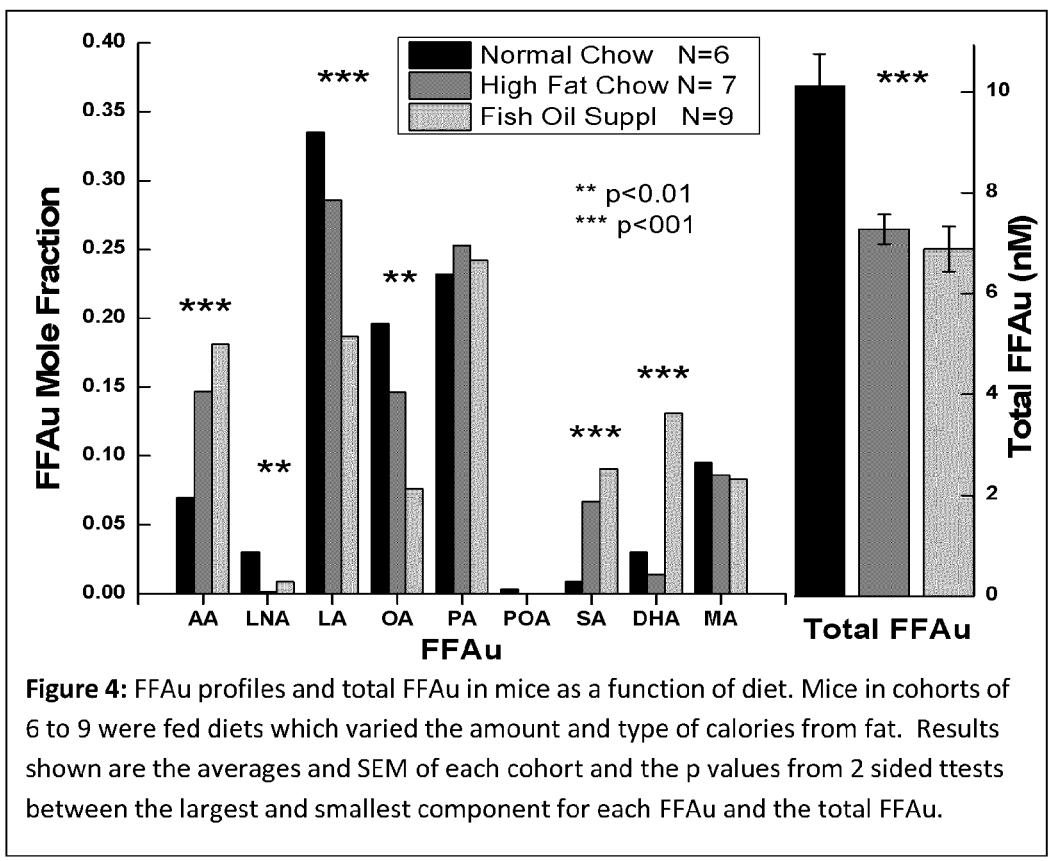
Figure 4: FFAu profiles and total FFAu in mice as a function of diet. Mice in cohorts of 6 to 9 were fed diets which varied the amount and type of calories from fat. Results shown are the averages and SEM of each cohort and the p values from 2 sided ttests between the largest and smallest component for each FFAu and the total FFAu.

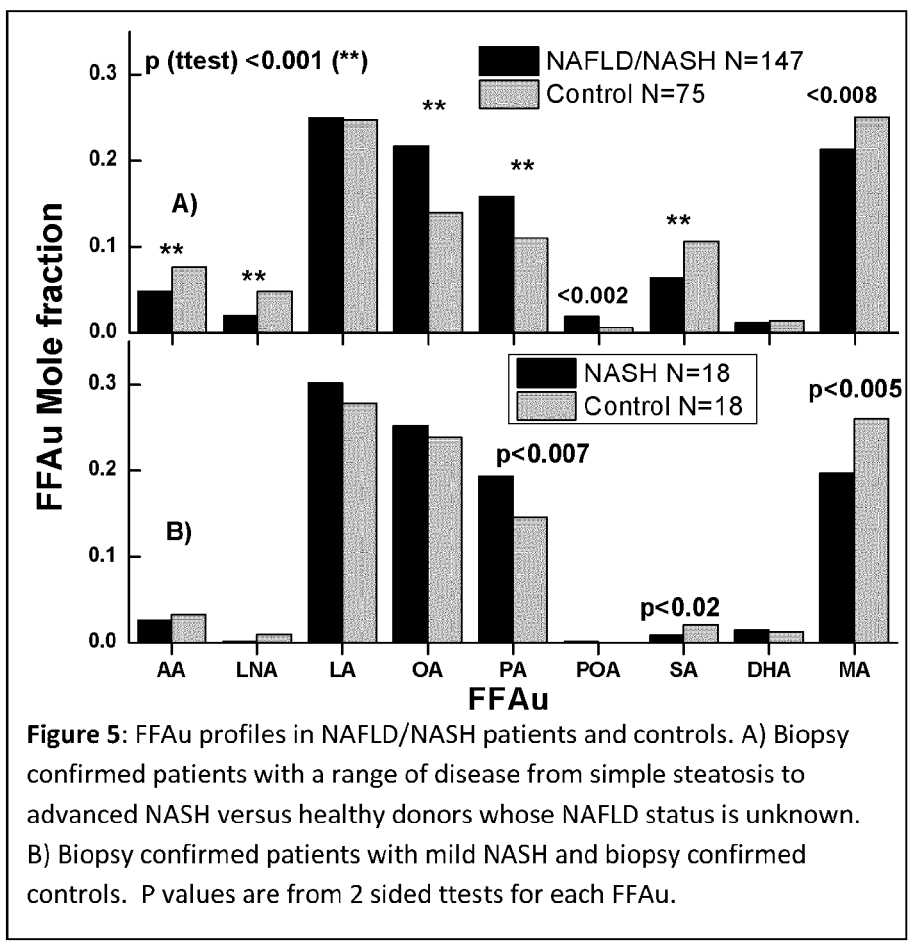
Figure 5: FFAu profiles in NAFLD/NASH patients and controls. A) Biopsy confirmed patients with a range of disease from simple steatosis to advanced NASH versus healthy donors whose NAFLD status is unknown. B) Biopsy confirmed patients with mild NASH and biopsy confirmed controls. P values are from 2 sided ttests for each FFAu.

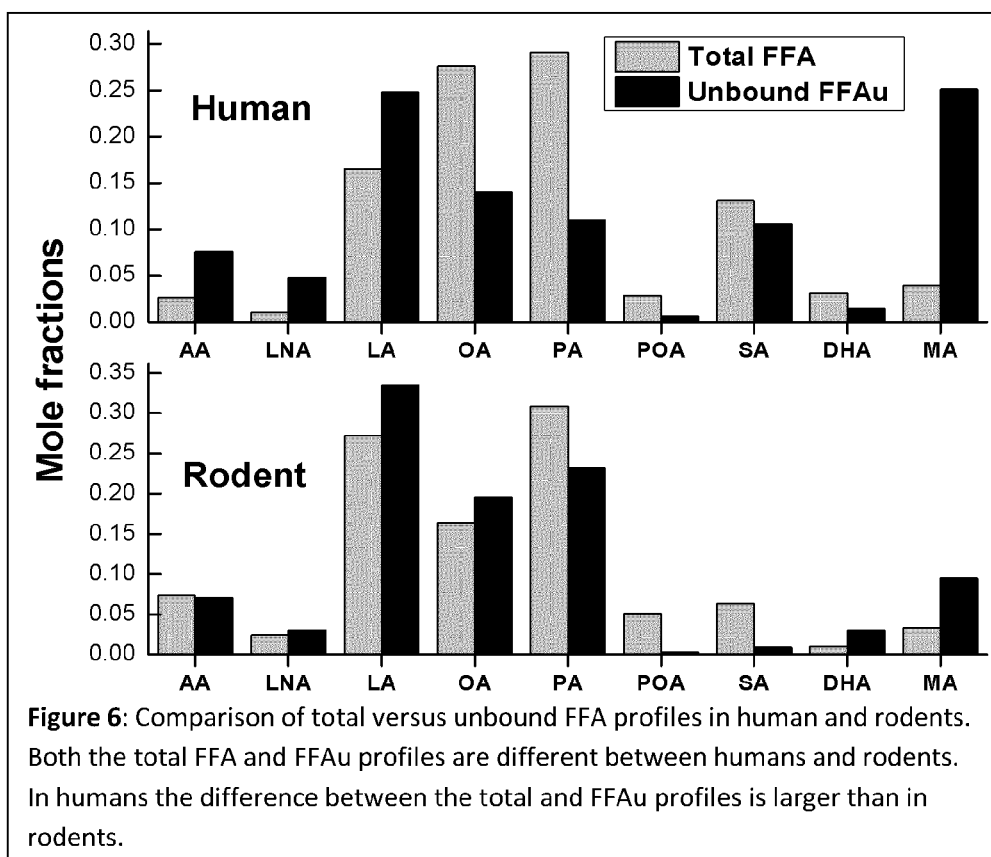
Figure 6: Comparison of total versus unbound FFA profiles in human and rodents. Both the total FFA and FFAu profiles are different between humans and rodents. In humans the difference between the total and FFAu profiles is larger than in rodents.

DETERMINATION OF THE UNBOUND FREE FATTY ACID PROFILES IN BIOLOGICAL AND INDUSTRIAL SPECIMENS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

This application incorporates by reference the sequence listing submitted as ASCII text filed via EFS-Web on May 19, 2016. The Sequence Listing is provided as a file entitled "FFASC75WO_SEQLST.TXT." created on Nov. 24, 2014, and which is approximately 2 kilobytes in size.

BACKGROUND OF THE INVENTION

Field of the Invention

The field of the invention relates to determination of the profile of unbound free fatty acids (FFAu) in biological samples, such as human and animal blood specimens and plant and animal oils, by measuring the fluorescence response of sets of different fluorescently labeled fatty acid binding proteins (probes) that undergo a change in fluorescence ratio at 2 wavelengths upon binding an FFAu. The field also relates to the use of these profiles in human and animal disease, in basic research, in drug development and in industrial uses.

Description of the Related Art

For purposes of the present disclosure, "fatty acids", are non-esterified carboxylated alkyl chains of 1-30 carbons atoms which may exist as neutral (e.g. protonated, sodium or potassium salt) or ionic species, depending upon the pH and conditions of the aqueous media. "Free fatty acids (FFA)" are equivalent to fatty acids and both terms refer to the totality of FFA including those in aqueous solution as monomers plus those that are not in solution (for example bound to other macromolecules (proteins, membranes), cells, oil droplets, or part of an aggregate of FFA (micelles, soaps and other more complex aggregates). FFA present as monomers in aqueous solution (either charged or neutral) are referred to as "unbound free fatty acids (FFAu)". For purposes of the present disclosure, FFA are molecules whose molecular weight ranges from about 70 to about 500 Da and FFAu are these molecules in aqueous solution.

For the purposes of the present disclosure, the term "lipid" is taken to have its usual and customary meaning and defines a chemical compound which is most soluble in an organic solvent but has some level of solubility in the aqueous phase (the fraction that is unbound). FFAs are a type of lipid and FFAu are that fraction of FFA that are soluble in the aqueous phase. Accordingly, a "lipid-binding protein" includes any protein capable of binding a lipid as lipid is defined herein.

Levels of unbound FFA provide information diagnostic of health and disease when measured in appropriate human or animal fluids (Richieri G V and Kleinfeld A M (1995) J Lipid Res 36: 229-240, Kleinfeld A M, et al. (1996) Am J Cardiol 78: 1350-1354, Cantor W J et al, (2008) J Invasive Cardiol 20: 186-188., Bhardwaj A, et al (2011). Am Heart J 162: 276-282, Hegyi T, et al (2013). Neonatology 104: 184-187, 2013. Huber A H, et al (2013) Am J Cardiol. 113:279-284. FFAu levels provide information essential to fundamental biology and have important applications in drug development and industry. It is increasingly apparent that determination of the unbound (a.k.a 'aqueous phase' or 'free') concentration of such molecules provides critical information about physiologic homeostasis. Many FFA are hydrophobic molecules with low aqueous solubility and unbound concentrations that are much lower than their "total" concentration, where the bulk of the "total" may be bound to proteins or cells. In biological fluids the concentration of the unbound FFA is often regulated to maintain a relatively constant unbound concentration under normal physiologic conditions. Much of this regulation occurs through the interaction of the molecules with a carrier protein such as for example, albumin. Thus most of the physiologically important medium and long chain FFA are generally bound to albumin, or other carriers. However a small fraction of the molecules may dissociate (and rebind to) from the albumin into the aqueous phase and these are the unbound molecules.

Intracellular lipid binding proteins (iLBP) are a family of low-molecular weight single chain polypeptides all of whom have similar 3 dimensional atomic structures. There are four recognized subfamilies. Subfamily I contains proteins specific for vitamin A derivatives such as retinoic acid and retinol. Subfamily II contains proteins with specificities for bile acids, eiconsanoids, and heme. Subfamily III contains intestinal type fatty acid binding proteins (FABPs) and Subfamily IV contains all other types of fatty acid binding protein (Haunerland, et al. (2004) Progress in Lipid Research vol. 43: 328-349). The entire family is characterized by a common 3-dimensional fold. Ligand binding properties of the different subfamilies overlap considerably. The wild type proteins of subfamily I (Richieri et al (2000) Biochemistry 39:7197-7204) and subfamily II both bind fatty acids as well as their native ligands. Moreover, single amino acid substitutions are able to interconvert the ligand binding properties of proteins of subfamilies I and II (Jakoby et al (1993) Biochemistry 32:872-878).

SUMMARY OF THE INVENTION

Embodiments of the invention are directed to methods for determining the profile of unbound FFA (FFAu) in a sample which includes one or more of the following steps:
(a) identifying a set of one or more FFAu specific probes;
(b) combining each probe with a separate aliquot of the sample;
(c) measuring a fluorescence index at two different emission wavelengths for each probe in the combined probe and aliquot of the sample;
(d) calculating the ratio of the fluorescence index at the two wavelengths for each probe in the sample;
(e) expressing each probe's ratio in terms of sum of contributions from the different FFAu to which the probes respond; and
(f) solving a set of ratio equations for the profile of the FFAu concentrations.

In preferred embodiments, the set of one or more FFAu specific probes includes probes with complementary specificities for the FFAu of interest and/or the FFAu in the sample.

In some preferred embodiments, the number of probes is equal to the number of FFAu to be solved for. Preferably, the set of ratio equations where the number of equations equals the number of FFAu has a unique solution for the FFAu profile.

In some preferred embodiments, more than one probe is used and the number of probes is greater than the number of FFAu to be solved for. Preferably, the FFAu profile is determined using a fitting method. Preferably, the fitting method is selected from curve fitting, least squares, and monte carlo methods. More preferably, the FFAu profile is determined using a least squares method.

In preferred embodiments, the total FFAu for each probe is presumed to be equal and the distribution that best fits this requirement is found by minimizing the overall least squares differences.

In preferred embodiments, the set of probes is selected from TABLE 2.

In preferred embodiments, the accuracy of the calibration of the probes is assessed by requiring the total FFAu ($FFA_u^T$) to be equal for each probe using equation (4) for each probe's $FFA_u^T$ for each probe j.

$$FFA_u^T = \frac{R^j - R_o^j}{\left(\left\langle\frac{Rm^j}{Q^j Kd^j}\right\rangle - R^j \left\langle\frac{1}{Q^j Kd^j}\right\rangle\right)} \quad (4)$$

Rj is the blank subtracted fluorescence intensity at wavelength 1 divided by the blank subtracted fluorescence intensity at wavelength 2 in the presence of each FFAu from 1 to N and N is the total number of FFAu; $R_o^j$ is the blank subtracted fluorescence intensity at wavelength 1 divided by the blank subtracted fluorescence intensity at wavelength 2 in the absence of each FFAu for each probe: Rm$^j$ is the R value at saturation. $Q^j$ is the is the ratio of the fluorescence intensity at wavelength 2 with no FFAu to the fluorescence intensity at wavelength 2 at saturation; $K_d^j$ is the equilibrium dissociation constant for probe j and each FFAu, and the brackets < > represent $\alpha_i$ weighted averages for the indicated quantities, wherein where the sum of $\alpha_i=1$.

Preferably, the $FFA_u^T$ values are calculated for each probe and the average value and standard deviation are calculated for the set of probes used to determine the FFAu profiles. Preferably, probes whose $FFA_u^T$ deviate significantly from the average are recalibrated and the FFAu analysis is repeated. Preferably, FFAu total is the same value for each probe.

In preferred embodiments, the FFAu profiles so obtained re used to diagnose disease in humans or animals.

In preferred embodiments, the FFAu profiles obtained are used to monitor disease progression in humans or animals.

In preferred embodiments, the FFAu profiles obtained are used to determine the risk of future disease in humans or animals.

In preferred embodiments, the FFAu profiles obtained are used to monitor effects of drugs in humans or animals.

In preferred embodiments, the FFAu profiles obtained are used to monitor effects of diet in humans or animals.

In preferred embodiments, the FFAu profiles obtained are used in research to determine the role of specific FFAu in cellular and biochemical pathways.

In preferred embodiments, the FFAu profiles obtained are used to screen cells and microorganisms for alterations in fatty acid pathways. Preferably, alteration of fatty acid pathways includes the production of specific oils.

In preferred embodiments, the FFAu profiles obtained are used to optimize enzymatic processes.

In preferred embodiments, the fluorescence index is intensity, polarization and/or lifetime of the probe, in the presence and absence of each analyte in the set of analytes of interest.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 2 shows FFAu profiles of rats infused with different oils and nicotinic acid. The 5 panels from top to bottom are: A: saline, B: nicotinic acid, C: nicotinic acid+safflower oil, D: nicotinic acid+olive oil, and E: nicotinic acid+coconut oil.

FIG. 3 shows effect of diet on rat FFAu profit s and total FFAu. The results show significant differences for AA, DHA, and MA. However, both diets yield overall similar profiles with LA being the major FFAu, about 3 fold larger than any other FFAu. Black bars indicate low fat diet and gray bars indicate high fat diet.

FIG. 4 shows FFAu profiles and total FFAu in mice as a function of diet. Mice in cohorts of 6 to 9 were fed diets which varied the amount and type of calories from fat. Results shown are the averages and SEM of each cohort and the p values from 2 sided t-tests between the largest and smallest component for each FFAu and the total FFAu. Black bars illustrate normal chow (N=6); dark gray bars illustrate high fat chow (N=7); and light gray bars indicate fish oil supplemented high fat chow (N=9).

FIG. 5 shows FFAu profiles in NAFLD/NASH patients acid controls. FIG. 5A shows biopsy confirmed patients with a range of disease from simple steatosis to advanced NASH versus healthy donors whose NAFLD status is unknown. FIG. 5B shows biopsy confirmed patients with mild NASH and biopsy confirmed controls. P values are from 2 sided t-tests for each FFAu. Black bars indicate NAFLD/NASH (N=147 (a) or N=18 (b)); Gray bars indicate Control (N=75 (a) or N=18 (b)).

FIG. 6 shows comparison of total versus unbound FFA profiles in human and rodents. Upper panel shows human profile; bottom panel shows rodent profile. Both the total FFA and FFAu profiles are different between humans and rodents. In humans the difference between the total and FFAu profiles is larger than in rodents. Black bars indicate FFAu profiles and grey bars indicate total FFA profiles.

DETAILED DESCRIPTION OF THE PREFERRED EMBODIMENT

Figure 1:
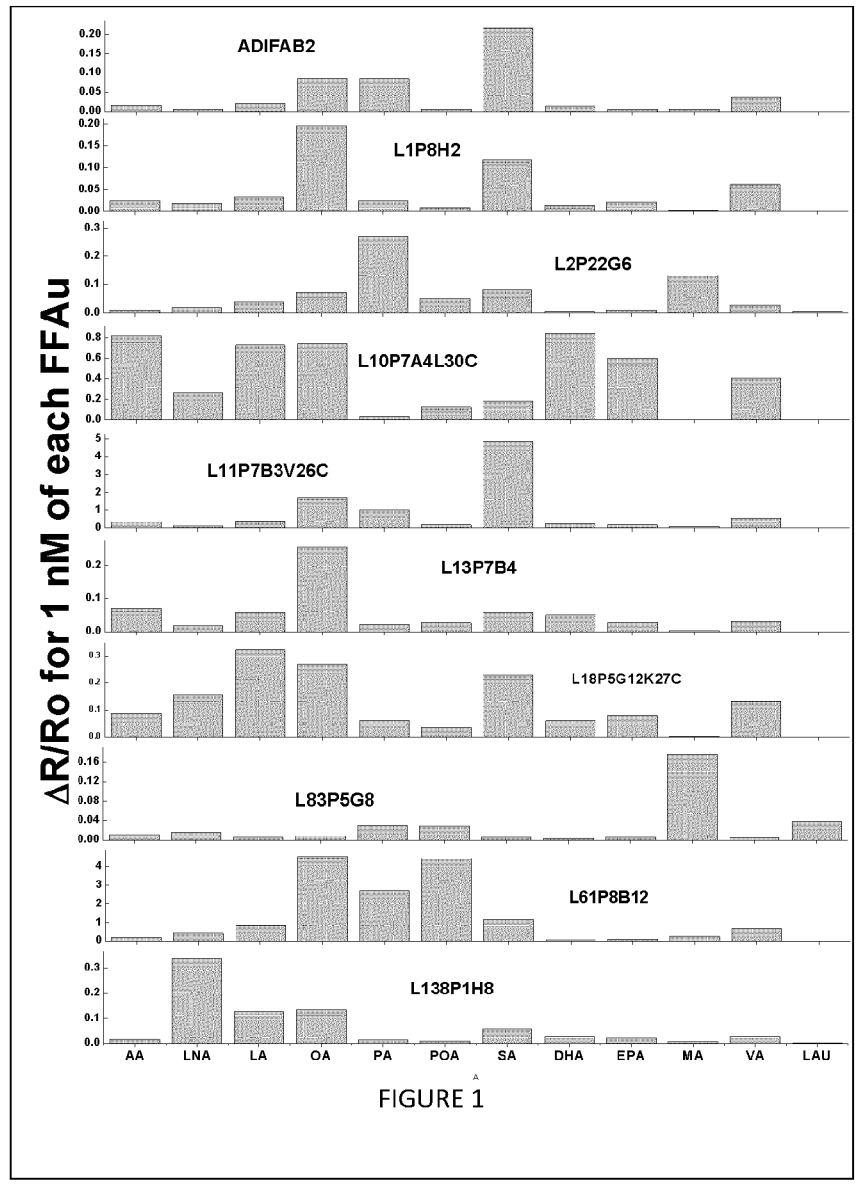
FIG. 1 shows examples of response profiles for several probes of Table 2 with complimentary specificities for different FFAu. The abbreviations are: arachidonate (AA), docosahexaenoate (DHA), eicosapentaenoate (EPA), laurate (LAU), linoleate (LA), linolenate (LNA), myristate (MA), oleate (OA), palmitate (PA), palmitoleate (POA), stearate (SA), and vaccenate (VA).

U.S. Pat. Nos. 5,470,714, 6,444,432, 7,601,510 and application US2010/0298162 all of which are incorporated herein by reference, describe probes for the determination of unbound free fatty acids (FFAu). These probes were constructed using either native or mutant forms of proteins from the iLBP family. As discussed above, this family includes FABPs (Banaszak et al (1994) Adv. Protein Chem. 45:89-151; Bemlohr et al (1997) Ann. Rev. Nutrition, 17: 277-

303). FABPs are intracellular proteins of approximately 15 kDa molecular weight and have a binding site that binds 1 or 2 FFA.

For the purposes of the present disclosure "probes" are iLBPs that are fluorescently labeled at a cysteine or lysine residue and that undergo a change in the ratio of a fluorescence index measured at different 2 wavelengths ($\lambda 1$ and $\lambda 2$) upon binding an analyte. In preferred embodiments, the excitation wavelength is 375 nm+/−20 nm, preferably +/−10 nm, more preferably +/−5 nm and the two emission wavelengths are 550 nm+/−20 nm, preferably +/−10 nm, more preferably +/−5 nm for $\lambda 1$ and 457 nm+/−20 nm, preferably +/−10 nm, more preferably +/−5 nm for $\lambda 2$. Such probes may be used to determine the aqueous concentration of specific unbound analytes including FFAu, which was not possible before the development of the FFAu probes due to the poor solubility properties of FFAs in aqueous solutions. In some preferred embodiments, the iLBP is a FABP.

Prior to the present invention, concentrations (also referred to as "levels") of FFAu were measured either with a known single or mixtures of molecular species of FFAu present in a sample or in a sample with an unknown mixture of different FFAu present. In all cases, these previous measurements used a single probe to estimate the concentration of the sum of all the molecular species of FFAu that were present and for which the probe had a measurable response (the "total FFAu"). In the case of an unknown mixture of different FFAu present, for example in a blood sample, a concentration of total FFAu was determined from the measurement using a single FFAu probe (Richieri G V and Kleinfeld A M (1995) J Lipid Res 36: 229-240). The total FFAu concentration determined by this measurement required an estimate of the FFAu distribution or profile, i.e. the relative concentrations of the different molecular species of FFAu present in the sample. The FFAu profile for the fatty acids being measured (major long chain FFA) could not be measured previously and was therefore estimated from the profile of the total FFA present, most of which, in a blood sample, would be bound to serum albumin. To estimate the FFAu profile, the total FFA profile was adjusted by the albumin binding constants for each FFA to yield an unbound FFA mixture averaged dissociation constant ($K_d^{mix}$) for the FFAu probe as described in (Richieri G V and Kleinfeld A M (1995) J Lipid Res 36: 229-240). Thus by this method the FFAu concentration in a mixture of FFAu is determined by multiplying the probe response by a constant ($K_d^{mix}$) irrespective of the sample type.

An important deficiency in determining the level or concentration of the total FFAu in a mixture, by the method of Richieri & Kleinfeld 1995 is that it assumes that the FFAu profile is the same in all samples and moreover it relies on the accuracy and constancy of the total FFA profiles. Although theoretical estimates, from albumin binding of FFA by Richieri & Kleinfeld 1995, of the effect of variations in the FFAu profile suggested relatively small changes in the total FFAu concentration, these estimates were based on calculations using a subset of 6 FFAu (which did not include MA, now known to have among the largest mole fraction), their measured albumin binding constants and the assumption that each FFA binds independently to albumin. However, it is unknown to what extent these assumptions apply accurately. Moreover, many non-FFA metabolites, hormones and drugs are known to bind to albumin and compete with FFA binding. In addition the albumin binding phenotype is known to be altered by metabolic processes and is known to be different for different albumin alleles (Peters T. *All about albumin* Academic Press, 1996). The effect of these factors can result in substantial changes in the FFAu profile but with no change in the total FFA profile. The results of the present invention put in doubt the validity of limiting calculations to 6 FFAu, the assumption of independent binding, the neglect of non-FFA molecules binding to albumin, the constancy of albumin binding affinities and the accuracy/constancy of total FFA profiles.

The profile or distribution of different FFA is expected to reflect the physiologic slate. Many studies have determined the profile of total (primarily albumin bound FFA) plasma or serum FFA. Such measurements are insensitive to the physiologically active components, the unbound FFA, whose concentrations are about one millionth ($10^{-6}$) of the total FFA concentrations. Aside from the issue that the total FFA is insensitive to the FFAu profile, the total FFA profile may itself be uncertain. Total FFA profiles generated for example by Gas or Liquid Chromatography (GC or LC) or GC or LC-mass spectroscopy (MS) requires extraction of the lipid component from a sample (e.g. blood plasma). Extraction is done using organic solvents to separate the lipid from the aqueous phase. However, because the organic/aqueous partition coefficient of different FFA can differ by orders of magnitude this separation distorts the sample's actual total FFA profile. Although standards are added to the sample to correct for such distortions in most instances only a single standard is used which does not accurately account for the wide differences in FFA solubilities. These and other factors lead to additional alterations so that the reported total FFA distribution may not accurately represent the actual sample total FFA distribution.

In addition to these intrinsic uncertainties, results of published total FFA distributions from different studies, on what are similar samples, reveal large, as much as 10 fold, profile differences. For example, in 7 different studies in which FFA distributions were measured and averaged over 10 to 100 healthy human subjects the mole fractions of the major FFA differed by about 3 fold while the less abundant FFA fractions differed by more than 10 fold (Nelson et al (1997) Lipids 32:427-433; Yli-jama et al (2002) J. Int. Med. 251:19-28; Puri et al Hepatology (2009) 50:1827-1838; Quehenberger et al J. Lipid Res. (2010) 51:3299-3305; Tomita et al Dig. Dis. Sci. (2011) 56:3045-3052; Yang et al (2012) Clin. Biochem. 45:127-133; Wang et al (2012) Neurobiol. Aging 33:1057-1066). As a particular example, the mole fraction of myristate (14:0), which is a minor component of the total FFA distribution, ranges from 0.15% to 4.5% in these studies. In contrast, myristate is a major fraction of the FFAu profile averaging 20 to 30% of the total FFAu (the sum of all the individual FFau) and the method of the present invention determines these fractions with uncertainties of <10% (Tables 3-5 and FIGS. 2-6).

This illustrates four critically important differences between the measurements of total and unbound FFA. First, the FFAu concentrations are about one millionth of the total FFA concentrations and therefore FFAu levels are undetectable to all methods that are used to determine the total FFA levels. The only known method for determining FFAu profiles is the method of the present invention, monitoring the response of multiple FFAu probes and converting the responses into FFAu profiles. Second, the unbound, physiologically relevant profiles are distinctly different from and are not simply related to the total FFA profiles, so that for example, the relatively minor total myristate fraction is a major FFAu fraction. Third, the determination of the FFAu profile, which does not involve any sample alteration, is much more precise than the total profile. As a consequence, changes in the physiological state which are readily determined by measuring the FFAu profile may be invisible in measurements of the total FFA profile. Fourth, because the albumin's affinity for FFA may change in the presence of other metabolites, hormones and drugs, the FFAu profile may change with no change in the total FFA profile.

Biological systems are composed of thousands of different molecular species of lipids. In spite of considerable effort to define and characterize the lipidome it remains unclear what the functions are of the thousands of different lipid molecules and how they change with changes in normal and pathologic physiology. This lack of understanding also applies to FFA, although there is considerable evidence for changes in the profile of total FFA due to alterations in nutrition, disease and pharmaceutical agents. However understanding how these changes in total FFA profiles are related to fundamental physiology may be deficient because the fraction of the total that has physiologic relevance is the unbound fraction. The unbound free fatty acids (FFAu) not the hound (mostly to albumin) FFA are the physiologically/pathologically active fraction of the total FFA. Albumin bound fatty acids do not cross cell membranes, do not bind to intra or extracellular FFA receptors (including binding proteins) and are not substrates for any of the steps involved in fatty acid metabolism. Only the FFAs that dissociate from albumin and become unbound are active. The FFAu and total FFA are also distinguished by their very different concentrations. In general FFAu concentrations are approximately $10^{-6}$ of total concentrations (roughly, FFAu are about 1 nM and total FFA about 1 mM). That the FFAu but not the total FFA are physiologically active is also apparent because the equilibrium dissociation constants (KA) for FFA receptors, binding proteins and FFA metabolic enzymes are on the order of nM ($10^{-9}$M) not mM ($10^{-3}$M). Clearly measurements of the total FFA profiles, especially given the large methodological uncertainties (factors of more than 3) as discussed above, cannot detect changes in FFAu which are on the order of less than 1 part in $10^6$ of the total FFA.

The FFAu profile (distribution of the different FFAu) is different from the total FFA profile (FIG. 6). Although the FFAu profile is a function of the total FFA profile, the FFAu profile is modulated by the different albumin binding constants (all in the nM range) for different FFA, the different oil-water partition coefficients in the presence of cells or lipid droplets, the competition between FFA, drugs and other metabolites that bind to albumin, metabolic alterations of albumin and albumin polymorphisms (Peters (1996) All about albumin, Academic Press). The binding constants for the different FFA differ by orders of magnitude and as a consequence the unbound profile can appear to have no relationship to the total profile. As an example myristate (14:0) typically represents from 0.1 to 5% of the total FFA profile but 20 to 30% of the FFAu profile in human plasma. Binding of myristate to albumin is much weaker than for example palmitate (16:0) which is about 30% of the total profile but about 15% of the unbound profile.

Therefore to understand the role FFA play in pathology and physiology the FFAu profile must be measured. For example, unbound oleate (18:1) but not albumin bound oleate inhibits the ability of cytotoxic lymphocytes to kill tumor cells (Kleinfeld A M and Okada C. (2005) J Lipid Res 46: 1983-1990). An additional example is the finding that transport of FFA into and out of cells is driven by the FFAu not total FFA (Carley A N and Kleinfeld A M (2011) J Biol Chem 286: 4589-4597). Furthermore, the FFAu profile cannot (easily) be calculated from the total because a) determination of the total profile is uncertain, b) accurate binding isotherms for all fatty acids and their interactions are unknown (for example Tables 4 & 5) and c) effects of binding of other metabolite and/or drugs on the FFAu profiles is unknown.

Although FFAu profiles were previously determined in aqueous solutions of FFA and bovine albumin (Huber et al Biochemistry (2006) 45:14263-14274) it was not known whether the Huber et al method would function correctly in biological samples. The method of Huber et al allowed the determination of FFAu profiles for mixtures of 5 or fewer FFA in aqueous solutions comprising bovine albumin and up to 5 different FFA. Samples of interest such as for example blood plasma and serum contain large numbers of potentially interfering molecules, including about 40 different FFA of which 9 to 15 would be expected to interact with the FFAu probes available to Huber et al. Moreover, because there is no other method for measuring the FFAu profile it was uncertain how to determine the accuracy of an FFAu profile determined in a biological sample with unknown FFAu profiles plus a rich environment of other potentially interfering molecules, such as albumin binding non-FFA metabolites, hormones and drugs.

Moreover, at the time of Huber et al only a limited number of FFAu specific probes were available. All of those FFAu probes were generated by labeling mutant FABPs with acrylodan at lysine 27 (SEQ ID NO: 1 without substitution at position 131). The ability to successfully profile human and animal blood samples, as described in this disclosure, is largely due to the use of cysteine-labeled probes as described in application US2010/0298162 which is incorporated herein by reference. The lysine-acrylodan reaction is inefficient and the labeling of FABP to make probes was only successful because lysine 27 was at a location very advantageous for the labeling reaction. Even with the lysine at position 27, many mutant FABP labeling reactions failed to run to completion. Thus, poor labeling efficiency prevented movement of the lysine (i.e. the labeling position) to other positions that might be more favorable for probe performance. Cysteine reacts very efficiently with acrylodan allowing movement of the labeling site to numerous locations around the binding pocket to find the position that provides the best combination of specificity and signaling. The use of cysteine labeling sites enabled the discovery of probes with much higher sensitivity and specificity than was available previously. Since these probes are nearly 100% labeled with acrylodan, the probe calibrations are more reliable, providing better determined probe performance parameters. For example, high affinity probes for myristate, which has among the largest FFAu mole fractions in human blood, and palmitoleate were only identified after switching to cysteine labeling. Because cysteine probes typically have significantly higher affinities for FFA, they are also more specific and will not response significantly when exposed to potential interfering compounds in blood (for example, non-FFA metabolites, hormones and drugs). Possible interference caused by other metabolites in biological fluids was a major concern when only lysine-labeled probes were being used.

Embodiments of the present invention solve the problem of determing accurate FFAu profiles in blood specimens as well as other biological fluids with no alteration of the sample. Embodiments of the present invention allow accurate determinations of FFAu profiles through 1) development of probes highly specific for individual FFAu, 2) using sets of 2 to 50, preferably 5 to 40, more preferably 10 to 30 FFAu probes with highly complementary specificities, 3) generating calibrations of each probe for 5, preferably 10, more preferably 15 different FFAu. 4) creating an algorithm that allows determination of the FFAu profiles from an over determined system and 5) validating the calibration for each of the probes used in the set used to determine the FFAu profile by requiring that each probe yield the same total FFAu. Validation of the results is made possible by in vivo and in vitro enrichment with specific FFA in animal and human blood samples with the demonstration that the specific FFA is enriched in the FFAu profile. In addition, measurements of FFAu profiles in hundreds of blood samples of physiologically similar (for example healthy individuals) showed similar FFAu profiles. Comparison with FFAu profiles from cohorts of unhealthy individuals that are significantly different than the healthy subjects, demonstrates the robustness and sensitivity of the FFAu profile determinations. The measurements involve simply, adding a probe to the sample and measuring its fluorescence ratio and repeating these steps for 2 or more different probes. Measurements of the FFAu profile involve virtually no modification of the sample, in contrast to the determination of the total FFA profile. The FFAu probes are the only method for measuring FFAu. Although, the measurements are simple, extracting the FFAu profiles from the fluorescence ratios requires a suite of FFAu probes with precisely characterized and complementary specificities for different FFAu. Continuous improvements of the FFAu probes increase the range of FFAu that can be profiled and improve the profile's accuracy.

That the FFAu profiles are determined accurately by the method of the present invention is determined by infusing into the blood circulation, of animals and potentially in human subjects, oil/lipid emulsions of known composition, together with heparin. The oils are hydrolyzed by lipoprotein lipases that are released from the capillary endothelial cells by heparin. This lipase activity releases FFAu from the oil that is characteristic of the oil's known composition. Comparing FFAu profiles determined before and after infusion allows determination of the oil composition overlayed on the plasma matrix. Comparing results with different oils and at different levels assesses the validity of the method for determining FFAu profiles in blood samples (for example FIG. 2). In addition to this in vivo supplementation of plasma with specific FFAu, in vitro supplementation of plasma samples with specific FFAu added as FFA:albumin complexes also demonstrates the accuracy of quantitation of specific FFAu in the matrix of all plasma FFAu (see for example Tables 3-5). The ability of the method to determine perturbations of the FFAu profile is revealed by the alterations in FFAu profiles from animals maintained on different feeding regimes, or animals treated with drugs that alter FFA profiles and by comparing FFAu profiles in animals and humans in different disease or physiologic states (for example FIGS. 2-4 & 6).

Embodiments of the invention are directed to a method for determining FFAu profiles which includes one or more of the following steps:

(a) acquiring a sample from a human, animal, reptile, fish, plant, microorganism, plant, agricultural product, oils or food;
(b) choosing a set of two or more FFAu probes with complementary specificities for different FFAu or a high degree of specificity for a single FFAu;
(c) calibrating each of the set of 2 or more FFAu probes for each of the FFAu of interest that might be in the samples;
(d) preparing at least two or more samples for each of the set of two or more FFAu probes;
(e) adding one of each FFAu probe to each sample or add the sample to an array of separated FFAu probes;
(f) observing in a sample a fluorescence index measured at two different wavelengths in the presence and absence of the probes;
(g) observing the ratio (Ro) of a fluorescence index measured at two different wavelengths of the probes in the absence of FFAu;
(h) calculating the ratio (R) of a fluorescence index measured at two different wavelengths of the probes in a sample by correcting for the fluorescence index at each wavelength from the sample in the absence of the probes;
(i) expressing the measured R for each FFAu probe as a sum of the contributions from each of the calibrated FFAu;
(j) using analytical (mathematical) methods to determine the FFAu profiles for each sample from the set of measured R values for each sample; and
(k) requiring that each probe used in the set to determine the FFAu profiles yields the same total FFAu.

The set of probes may contain 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more probes in the set.

In some embodiments the samples and probes are added to cuvettes and the fluorescence index at two emission wavelengths are measured individually in a fluorometer.

In preferred embodiments the samples and probes are added to multi-well plates and the fluorescence index at two emission wavelengths are measured in a fluorescence plate reader.

In other preferred embodiments the probes are dried in the wells of multi-well plates, samples are added (also wells for zero FFA (Ro) and wells for samples without probes for background (blanks) and the fluorescence index at two emission wavelengths are measured in a fluorescence plate reader.

In other preferred embodiments the probes are dried at separate positions on a surface or a cartridge or a strip and a sample is added that flows across and fills the surface (also positions without probes for background (blanks)) and the fluorescence index at two emission wavelengths are measured in a fluorescence plate or cartridge reader. The Ro for the plate or cartridge is determined separately for each lot of plate or cartridge.

In preferred embodiments of the invention, the sample used for the determination of unbound FFA is a fluid sample derived from a human, an animal, a plant or cells. Preferably, the fluid is whole blood, blood plasma, blood serum, urine, CSF, saliva, gastric juices, interstitial fluid, lymph, an oil emulsion, cell extracts or cell medium. In some embodiments, unbound metabolites such as unbound FFA are extracted from tissue samples by means known in the art.

In preferred embodiments of the invention, the mathematical analysis is performed using the following equations relating the measured R (the blank subtracted intensity at 550 nm divided by the blank subtracted intensity at 457 nm) and Ro values of the probes to the calibration of each probe for each FFAu that is expected to produce a measurable response (see for example. FIG. 1) and to the concentration of the individual FFAu:

$$R^j - R_o^j = \sum_{i=N} \frac{FFA_i}{Q_i^j Kd_i^j}(Rm_i^j - R^j) \tag{1}$$

This is one equation for one probe ($R^j$) of the set of equations for n probes used to determine the profile of N FFAu. Where the concentration of each FFAu ($FFA_i$), in the sum multiplies a ratio that includes the calibration parameters for each FFAu of the jth probe as well as $R^j$. For each probe there are 3 calibration parameters for each $FFA_i$, $Rm_i^j$ is the R value at saturation, $Kd_i^j$ the equilibrium dissociation constant and $Q_i^j$ is the ratio of the intensity at 457 nm with no FFAu bound to that at saturation. The set of n equations, for all probes used in the measurements, together with the measured R and Ro values is used to determine the FFAu profiles $\{FFA_1, FFA_2, \ldots FFA_N\}$ by least squares fitting implemented for example in MLAB, MATLAB, or Solver in Excel.

While the described embodiment represents the preferred embodiment of the present invention, it is to be understood that those skilled in the art can modify the process without departing from the spirit of the invention.

Preferably, for the determination of an FFAu profile in a sample of 2 or more probes with complimentary specificities for the different FFAu that may be in the sample are chosen. Two or more replicates of the sample are aliquoted in the wells of a mult-well plate and the fluorescence intensities at two wavelengths are measured in each well to determine the blank intensities (the background intensities of the sample without probe added). To each of the 2 or more replicates wells, 2 or more different probes are added and the fluorescence intensities with the probes present at the two wavelengths are measured in each well. After subtracting the blank intensities at each wavelength the intensity ratios at the two wavelengths are evaluated for each probe. The measured R values together with the corresponding Ro values (R for zero FFAu) are used to solve equation 1 for the individual FFAu (FFAi) and thereby determine the FFAu profile.

Probes: U.S. Pat. Nos. 5,470,714, 7,601,510 and application US2010/0298162 which are incorporated herein by reference, describe probes for the determination of unbound free fatty acids (FFAu). Such probes with complementary specificities for different FFAu are used by the present invention to determine FFAu profiles, the concentrations of the individual FFAu in a sample. Probes can be highly selective for a single FFAu and can be used singly to determine the concentration of specific FFAu in a sample and can also be used together with less selective probes to determine accurately the profile of a mixture of different FFAu. Probes that are not absolutely specific for individual FFAu can determine the FFAu profile when combined with probes that have FFAu specificities that are complementary. Using multiple complementary probes that may exceed the number of FFAu for which a profile is sought generates an over determined condition for the solution of equation 1 and then the solution is found by curve fitting algorithms.

The set of probes chosen to determine the profile of a sample depends upon the nature of the sample, the types of FFA expected to be present in the sample and the determination that the chosen probes respond to the expected FFA. In addition, especially for the least abundant FFAu in a sample, the probe's sensitivity for a given FFAu must be sufficient to accurately quantitate the low concentration FFAu, for example less than 50 pM. Sensitivity is a function of the Kd, Q, Ro and Rm parameters. Differences in sensitivity among different FFAu probes are apparent in FIG. 1 where for example for ADIFAB2 (acrylodan labeled at lysine 27), 1 nM of SA produces a 20% increase in R while for L11P7B3V26C the increases is almost 500%. Thus the L11 probe whose Kd for SA is 250 pM would be chosen over ADIFAB2 (Kd 9.3 nM) to determine accurately low concentrations of SA (for example <50 pM). In the absence of absolutely specific and sensitive probes the determination of FFAu profiles requires an over determined system, which empirically requires about twice the number of probes as FFAu to obtain accurate profiles. The identity of the set of probes to achieve accurate FFAu profiles is not unique. Different combinations of probes can achieve similarly accurate profiles so long as the set includes probes with sufficient sensitivity and complementary specificities for all the FFAu to be profiled.

Calibration: Each probe is calibrated to the extent that the constants in Equation 2 are well determined for all FFAu to be included in profile calculations. Equation 2, which is the form of equation 1 for a single FFAu, relates the FFAu concentration to the equilibrium dissociation constant (Kd), fluorometric constants (Q and Rm) and the measured R values.

$$[FFA_u] = K_d \cdot Q \cdot \frac{(R - R_0)}{(R_m - R)} \tag{2}$$

The calibration parameters are determined essentially as described in U.S. Pat. No. 7,601,510 which is incorporated herein by reference and (Huber et al Biochemistry (2006) 45:14263-14274) where the calibrated ADIFAB2 probe was used to generate FFA-BSA complexes with accurate and well buffered FFAu concentrations. To calibrate probes with substantially higher affinities than used in U.S. Pat. No. 7,601,510 and (Huber et al Biochemistry (2006) 45:14263-14274) a boot strap method is used in which a probe having higher affinities is calibrated with ADTFAB2. Such a probe is then used to generate FFA-BSA complexes with FFAu concentrations from 0.1 to 10 nM and these complexes are then used to calibrate other high affinity probes. For example L61P8B12 has affinities and dynamic ranges for many of the FFAu that are typically between 50% and 50 fold larger than those for ADIFAB2 (Table 1).

Probe calibration involves titrating the probes with either (i) un-buffered FFA or (ii) BSA-buffered FFA stocks. The un-buffered titrations involve measuring the R-value of a 1 µM probe solution as it is slowly titrated to saturation with small aliquots of a 100 to 250 µM FFA stock (Richieri G V et al. (1992) J Biol Chem 267: 23495-23501, Richieri G V et al. (1999) Mol Cell Biochem 192: 87-94). In this case, the total FFA concentration for each point in the titration is known and a nonlinear fit to the titration data yields the full set of fluorometric constants. In an un-buffered FFA titration, probe concentration is a key variable because the probe binds FFA, directly affecting the FFAu value.

Alternatively, in a BSA-buffered FFA calibration, the probe solution is titrated with a series of FFA-BSA complexes (600 µM BSA with [FFAu] ranging from 0.1 nM to 4 µM). The titration samples are FFA-BSA complex diluted 50-fold in Measuring Buffer. Probe is added to a concentration of 0.5 µM and the R-value is measured. Because BSA buffers FFAu, its concentration remains constant (i.e. known), even after the addition of probe. A non-linear fit, which does not include probe concentration, yields the fluorometric constants. At least two calibrations with each of the up to 15 different FFA are performed for each probe.

An additional restriction on the FFAu profiles obtained from the least squares fitting with a set of n probes is to require that with the found FFAu profile, each probe must yield the same total FFAu (sum of the individual FFAu concentrations, see equation (4)). An iterative process is used in which a set of probes is calibrated, the FFAu distribution is analyzed, which probes yield FFAu totals that are substantially different than the average is determined, those probes are recalibrated, and the FFAu analysis is repeated. Alternatively, the outlier probe is removed to determine which FFAu is altered, the outlier probe is recalibrated for that FFAu and the FFAu analysis is repeated.

Fluorescence measurements: Fluorescence measurements are typically performed using an instrument capable of measuring two emission wavelengths from each well of multi-well plates the sample compartment maintained at about 22°±2° C. Several configurations of plate scanning fluorometers are commercially available. These include instruments that scan an entire plate at one emission wave length and repeat the scan at the second emission wavelength. Alternatives are instruments that scan by measuring each well with both wavelengths by switching wavelengths with a monochromater, by using a filter wheel, by using two emission monochromaters each at a different fixed wavelength or by using a dual emission configuration with two fixed filters. Typically, excitation of the probe fluorescence is carried out at wavelengths between 360 and 390 nm. Emission at the first wavelength is measured at between 450 and 470 nm and between 540 and 560 nm at the second emission wavelength. Band widths for both excitation and emission wavelengths are generally less than 10 nm.

Measurements of the sample blanks (without added probe) are performed first, together with measurements of the measuring buffer (20 mM HEPES, 140 mM NaCl, 5 mM KCl, and 1 mM $Na_2HPO_4$ at pH 7.4) which is used to dilute samples and fatty acid free albumin for measurements of Ro. Measurements are repeated after the probes are added and mixed with the sample and the fatty acid free albumin.

Samples: Most samples can be measured substantially diluted in measuring buffer. Dilution reduces the amount of sample needed, the level of potential background fluorescence and potential probe interferents. Dilution is limited by the ability of the diluted sample to buffer FFAu, especially in the presence of probe. The degree of allowable dilution is determined by measuring the effect of dilution on the R value for each probe. The buffering capacity is increased by increasing the sample concentration and/or diluting the probe concentration.

Typically for human or animal plasma or serum the samples are diluted 50 fold (2% sample) in measuring buffer and the probe concentration is less than 1 µM. At these concentrations FFAu is well buffered and the signal (fluorescence of the sample plus probe at both emission wavelengths) to background (fluorescence without probe (blank)) is greater than 10 to 1.

Analysis, determination of FFAu profiles from R values: The first step in the analysis is the determination of the level of uncertainty in the R values generally from 4 replicate measurements. Simulation of the degree to which random errors of increasing magnitude alter the derived profile indicate that the uncertainty in the average R values should be less than about 2%. Above 2%, deviations from 0 error become substantial and these deviations are different for different FFAu (Table 1).

TABLE 1

In these simulations equation 1, with 15 probes, was used to generate R values for the 0 error profile. Twenty copies of the set of R values were randomly altered by between 1 and 10%. FFAu profiles were derived for each copy of the R values for the 15 probes and the average values of the 20 profiles for each degree of error are shown in the Table.

| % error | Total | AA | LA | OA | PA | POA | SA | DHA | MA |
|---|---|---|---|---|---|---|---|---|---|
| 0 | 1.498 | 0.115 | 0.258 | 0.137 | 0.108 | 0.047 | 0.096 | 0.019 | 0.220 |
| 1 | 1.502 | 0.113 | 0.262 | 0.136 | 0.107 | 0.046 | 0.094 | 0.019 | 0.222 |
| 2 | 1.497 | 0.118 | 0.255 | 0.128 | 0.108 | 0.059 | 0.101 | 0.018 | 0.213 |
| 5 | 1.430 | 0.130 | 0.243 | 0.122 | 0.131 | 0.074 | 0.098 | 0.018 | 0.185 |
| 10 | 1.386 | 0.158 | 0.137 | 0.115 | 0.039 | 0.145 | 0.187 | 0.077 | 0.144 |

With R values for each sample and FFAu probe conforming to coefficients of variation (CVs) <2%, they are entered into a program that finds the best set of FFAu that solves the set of equations (1). Many commercially available software packages can be used, including for example, MLAB (Civilized Software), Matlab (Mathworks) and Solver in Excel. MLAB for example uses the Marquardt-Levenberg curve fitting method to solve the equations (1) for the FFAu profiles.

In addition to the effect of R value errors (CVs) on the accuracy of the FFAu profiles derived from the fit to equation (1), errors in the probe calibrations can also introduce uncertainties in the FFAu profiles. To assess the possibility of a calibration error, individual total FFAu estimates are calculated from the data for each probe and discrepancies between the total FFAu values for different probes are analyzed. The total FFAu should be the same for each of the probes used in the analysis if their individual calibrations are accurate. The total FFAu, comprising N types of FFAu, is given by equation (3), $$FFA_u^T = \Sigma_{i=1}^N FFA_i = FFA_u^T \Sigma_{i=1}^N \alpha_i \qquad (3),$$

where the sum of $\alpha_i = 1$.

Using this expression, equation (1) can be solved for $FFA_u^T$ as, $$FFA_u^T = \frac{R^j - R_o^j}{\left(\left\langle \frac{Rm^j}{Q^j Kd^j} \right\rangle - R^j \left\langle \frac{1}{Q^j Kd^j} \right\rangle\right)}, \qquad (4)$$

for each probe j, where the brackets < > represent $\alpha_i$ weighted averages for the indicated quantities. The $FFA_u^T$ values are calculated for each probe and the average value and standard deviation is calculated for the set of probes used to determine the FFAu profiles. Probes whose $FFA_u^T$ value differs substantially (for example, >2 standard deviations) from the average are indentified and re-calibrated. The FFAu profiles are re-analyzed using the re-calibrated outlier probe(s).

EXAMPLE 1

Examples of probes used, generally in groups of 10 or more, to determine FFAu profiles in biological samples such as blood plasma or serum from animals and humans or media from microorganisms are shown in Table 2. In the sequences presented in Table 2 and the sequence listing, amino acids are numbered from the first residue of the mature protein. The initiator methionine residue of the wild-type protein is removed by aminopeptidase activity, leaving an alanine as residue 1. Thus, counting backwards and skipping 0, the initiator methionine is at residue position −1. All probes were labeled with acrylodan at either lysine 27 or at the cysteine position listed in the table. Specificity indicates the FFAu that gives the largest response to 1 nM of each FFAu when one FFAu dominates the profile and more than one when there is a more even distribution of specificity. Where more than one is indicated they are listed in order of degree of specificity. The abbreviations are: arachidonate (AA), docosahexaenoate (DHA), eicosapentaenoate (EPA), laurate (LAU), linoleate (LA), linolenate (LNA), myristate (MA), oleate (OA), palmitate (PA), palmitoleate (POA), stearate (SA), and vacsinate (VA). The sequences indicate mutations relative to SEQ ID NO: 1. This sequence is a mutated rat intestinal fatty acid binding protein with a Glu 131 to Asp substitution and includes a COOH-terminal affininity tag comprising Arg 32, Gly 133 and 6 histidines.

TABLE 2

Examples of probes used for determining FFAu profiles

| Probe | Specificity | Sequence |
| --- | --- | --- |
| AD2 | SA | L72A |
| L1P8 H2 | OA/SA/VA | Y14M, L38M, L72W |
| L2WP22 G6 | PA | M18I, G31Y, A73G |
| L2P22 G6, K27C | PA | M18I, K27C, G31Y, A73G |
| L4BP4 B9 | PA/MA | L72A, A73W, C74S |
| L9BP6 H3 | SA/OA/PA | L38Y, F62W, L72A, Y117A |
| L10P7 A4 | AA/DHA/OA/EPA/LA | Y14L, M18L, G31Y, A73L, Y117A |
| L10P7 A4, L30C | AA/DHA/OA/EPA/LA | Y14L, M18L, K27A, L30C, G31Y, A73L, Y117A |
| L11P7 B3 | SA | M21F, L72A, L78V, L102V |
| L11P7 B3, L102L | SA | M21F, L72A, L78V |
| L11P7 B3, V26C | SA | M21F, V26C, L72A, L78V, L102V |
| L13P7 B4 | OA | L72A, R108W, Q115C |
| L13EP16 E11 | OA | V28C, K27A, V49L, L72A, R106W, Q115S |
| L18P5 G12 | LNA/LA/OA/SA/VA | Y14R, M18L, A73F, Y117D, A72L |
| L18P5 G12, K27C | LNA/LA/OA/SA/VA | Y14R, M18L, K27C, A73F, Y117D, A72L |
| L19CP4 H9 | LA | M-1G, A1I, Y14R, M18L, K27C, L72A, A73F, Y117D |
| L19CP10 C7 | LA | M-1G, A1I, Y14R, M18L, K27C, S71I, A73F, Y117D |
| L22P5 E11 | SA/OA/LA | L38A, A69T, L72A, A73K, R108A |
| L33P3 F9 | DHA/AA | M18L, I23L, G31N, L72W, A73T, D74A, R106A, Q115E, Y117V |
| L35P10C4 | DHA/AA | M18L, G31N, L36Y, L72W, A73T, D74A, R106A, Q115E, Y117V |
| L35P22E8 | DHA/AA | M18L, I23L, G31N, L36R, L38V, L72W, A73T, D74A, R106A, Q115E, Y117V |
| L36P15 B7-1 | HA/AA/EPA | M18L, I23V, G31N, F55R, L72W, A73T, D74A, R106A, Q115E, Y117V |
| L37P1 C3 | AA/DHA/EPA | Y14W, M18L, M21I, I23L, G31N, L38V, L72W, A73T, D74A, R106A, Q115E, Y117V |
| L44P1 C10 | PA/OA/SA | Y14L, M18L, I23L, G31N, L72G, A73T, D74A, R106W, Q115W, Y117L |
| L50AP31 A2 | MA | M18L, I23L, K27A, L30C, G31N, L72S, A73T, D74A, T78V |
| L50BP4 E2 | PA/MA | M18L, M21F, I23F, K27C, G31N, L72T, A73T, D74A, T76F |
| L50BP9 D5 | PA/POA/MA | M18L, M21F, I23L, K27C, G31N, L72S, A73T, D74A, T76I, Y117N |
| L61P8 B12 | POA/OA/PA | M8I, Y14L, M18L, I23L, K27Y, L30C, G31V, S53I, F55W, L72G, D74A, L76V, W82V, G91Y, F93M, L102V, R106W, Q115W, Y117L |
| L68P3 H10 | DHA | M18L, I23A, K27C, G31N, H33N, F55Q, L72W, A73T, D74L, T78I, R106A, Q115E, Y117V |
| L68P6 B7 | DHA/AA | M18L, I23P, K27C, G31N, H33N, F85T, L72W, A73T, D74V, T78I, R108A, Q115E, Y117V |
| L71AP22 B3 | AA/DHA/EPA | Y14W, M18L, M21I, I23L, V28C, K27A, G31N, L38V, F55S, L72W, A73T, D74S, T78P, R106A, Q115E, Y117V |
| L71BP33 D1 | DHA/AA/EPA | Y14W, M18L, M21I, I23Y, K27C, G31N, L38V, L72W, A73T, D74F, T78P, R106A, Q115E, Y117V |
| L76P9 E4 | OA/VA/SA/LA | Y14L, M18Y, I23T, K27L, L30C, G31I, L72G, A73I, D74A, L78V, W82P, G91S, F93M, A104F, R106L, Y117L, Q115A |
| L76P20 A7 | OA/EA/VA | Y14L, M18Y, I23T, K27L, L30C, G31I, L72G, A73I, D74A, L78V, V82M, F93M, 102L, A104H, R108L, W115S, Y117L |
| L83P5 G8 | MA/LAU | M-1G, A1I, M18L, M21F, I23T, K27C, G31N, V49G, L72T, A73T, D74A, T76V, Y117H |
| L85P1 C2 | LNA/LA/OA | M-1G, A1I, M18L, M21L, I23Y, K27C, G31N, L72T, A73T, D74A, T76V, Y117H, F128Y |
| L106P3 B10 | MA | M-1G, A1L, M18L, M21F, I23H, K27C, G31N, L72T, A73T, D74A, T76P, L78I, A104S, Y117H, F128Y |
| L106P10 G10 | PA/MA | M-1G, A1I, M18L, I23L, K27C, G31N, L38V, L72T, A73T, D74A, T76I, L102I, A104S, Y117H, F128Y |
| L118P4 H5 | DHA | Y14W, M18Q, K27C, L72A, D74Q, R106W |
| L119P3 E5 | PA | M18V, K27C, G31A, L72A, A73W |
| L127P3 G2 | AA | Y14W, M18E, M21V, I23L, K27C, G31N, L38V, F55R, L72W, A73T, D74A, L78W, R106A, Q115E, Y117V |
| L128P18 A7 | DHA/AA | Y14W, M18L, M21I, I23L, K27C, G31G, L38V, S71M, L72W; A73T, D74P, A104I, R106A, Q115E, Y117V |
| L138P1 H8 | LNA | M-1G, A1I, M18L, M21L, I23Y, K27C, G31I, F55V, L72S, A73S, D74G, T76V, Y117H, F128Y |
| L138P1 H8, N24C | LNA | M-1G, A1I, M18L, M21L, I23Y, N24C, G31I, F55V, L72S, A73S, D74G, T78V, Y117H, F128Y |
| L156P3 F9, V26C | POA/OA/PA | Y14L, M18L, I23T, V28C, K27F, L30C, G31A, L72G, D74A, L78T, W82V, G91Y, F93M, L102V, R106W, Q115W, Y117L |

EXAMPLE 2

Table 3 shows examples of calibration constants for selected FFAu probes of Table 2. Calibrations were determined as described in [0065] and the abbreviations are given in Table 2. All of the probes reveal substantial differences for different FFAu and in many cases these differences are related to the aqueous solubility of the FFA. For example, of the FFA in Table 3, SA is the least soluble and MA the most soluble. As discussed in (Richieri G V et al (2000) *Biochemistry* 39: 7197-7204) the tendency of natural proteins and FABPs, in particular, is for binding constants to be largest (smallest Kd) for the least soluble FFA and conversely for the most soluble FA. In two cases, ADIFAB2 and L11, Kd for SA is substantially the smallest and MA the largest and that pattern is more or less maintained for most of the other probes in Table3 with the exception of L83. In that case MA has the largest affinity while SA's more than 10 fold smaller. To some extent the other calibrations constants follow that behavior; Q is largest for the smallest Kd and Rmax is often largest, so that the probe response tends to be larger for FFA with the larger affinities. The ability to generate mutations that overcome the "natural thermodynamics" allows for probes that have a wide range of specificities and sensitivities than enable the determination of FFAu profiles.

a single FFAu. However all the probes have different profiles and therefore complementary specificities for different FFAu. Abbreviations are as in Table 2.

EXAMPLE 4

The effects of nicotinic acid (NA) and different oil infusions on the FFAu profiles in rat plasma was measured as a demonstration of the validity of the profiling method (FIG. 2). Results are averages of 7 animals for each condition. Nicotinic acid inhibits hormone sensitive lipase (HSL) in adipose tissue resulting in a reduction in circulating FFA levels. Whereas infusion of emulsions of oils of different compositions, together with heparin to activate lipoprotein lipase, will result in the increase of plasma FFA that reflect the composition of the infused oils. When infused together NA and oils results in FFAu profiles that are a conflation of the two effects. The control profile (saline) indicates that LA is the dominant fraction at 40% and both AA and PA are larger than OA. Adding NA reduces all FFAu except AA which becomes the dominant fraction at nearly 50%. This suggests that plasma AA is not governed by HSL and is consistent with total FFA profile results in humans (Hagenfeldt L et al (1972) *J Clin Invest* 51: 2324-2330) Adding NA plus Safflower oil (whose dominant fatty acid is LA)

TABLE 3

Examples of calibration constants for probes listed in Table 2

|    |     | ADIFAB2 | L1P8 H2 | L2P22 G6 | L10P7 A4 L30C | L11P7 B3 V26C | L13P7 B4 | L18P5 G12 K27C | L83P5G8 | L61P8B12 | L138P1 H8 |
|----|-----|---------|---------|----------|---------------|---------------|----------|----------------|---------|----------|-----------|
| Ro |     | 0.087   | 0.620   | 0.200    | 0.260         | 0.191         | 0.085    | 0.401          | 0.302   | 0.044    | 0.522     |
| Kd | AA  | 167.3   | 104     | 90.6     | 1.0           | 6.1           | 35.9     | 9.1            | 923.5   | 107.1    | 118.9     |
| (nM) | DHA | 253.0 | 248.3   | 206.2    | 1.2           | 7.5           | 59.8     | 10.4           | 1082.8  | 238.1    | 171.0     |
|    | LNA | 236.7   | 217     | 89.0     | 2.7           | 11.2          | 149.0    | 4.1            | 161.4   | 46.3     | 6.5       |
|    | LA  | 100.9   | 97.5    | 42.2     | 1.1           | 3.9           | 46.4     | 2.1            | 138.6   | 22.1     | 10.7      |
|    | OA  | 32.0    | 14.4    | 33.9     | 1.3           | 1.0           | 10.5     | 3.0            | 132.4   | 4.1      | 10.7      |
|    | PA  | 21.4    | 45.4    | 5.6      | 3.0           | 1.1           | 46.7     | 8.2            | 21.8    | 9.8      | 41.6      |
|    | POA | 257.0   | 209     | 87.9     | 5.5           | 11.1          | 90.3     | 24.4           | 42.6    | 4.7      | 81.6      |
|    | SA  | 9.3     | 19.2    | 17.6     | 2.0           | 0.25          | 45.2     | 2.8            | 99.5    | 21.3     | 18.7      |
|    | MA  | 324.0   | 298.8   | 47.8     | 15.4          | 18.8          | 151.5    | 426.3          | 8.7     | 91.9     | 233.2     |
| Q  | AA  | 5.0     | 0.24    | 2.8      | 11.2          | 27.0          | 2.2      | 9.7            | 30.4    | 2.4      | 1.5       |
|    | DHA | 3.3     | 0.28    | 3.4      | 15.8          | 27.4          | 2.4      | 7.1            | 3.7     | 1.4      | 1.6       |
|    | LNA | 5.0     | 0.27    | 3.8      | 6.7           | 21.8          | 1.8      | 10.7           | 35.1    | 6.6      | 8.1       |
|    | LA  | 4.0     | 0.25    | 2.6      | 8.2           | 23.1          | 1.9      | 11.1           | 361.6   | 5.8      | 6.0       |
|    | OA  | 5.0     | 0.20    | 2.4      | 4.9           | 25.7          | 2.2      | 8.9            | 5.7     | 7.4      | 2.9       |
|    | PA  | 6.6     | 0.44    | 4.0      | 1.5           | 21.4          | 1.7      | 5.5            | 17.2    | 10.1     | 1.6       |
|    | POA | 4.5     | 0.47    | 2.7      | 2.9           | 17.5          | 1.8      | 7.1            | 27.6    | 12.2     | 2.4       |
|    | SA  | 6.6     | 0.34    | 3.0      | 2.5           | 29.0          | 1.8      | 9.8            | 2.2     | 8.3      | 1.6       |
|    | MA  | 3.7     | 0.76    | 3.3      | 1.0           | 10.5          | 2.5      | 2.3            | 22.6    | 7.1      | 1.8       |
| Rm | AA  | 0.91    | 0.08    | 0.83     | 2.5           | 8.3           | 0.57     | 2.7            | 10.6    | 2.4      | 0.7       |
|    | DHA | 0.64    | 0.18    | 1.13     | 3.2           | 8.7           | 0.58     | 2.0            | 1.2     | 1.3      | 1.1       |
|    | LNA | 0.80    | 0.06    | 1.21     | 1.4           | 5.9           | 0.50     | 2.9            | 8.9     | 6.6      | 4.2       |
|    | LA  | 0.73    | 0.08    | 0.99     | 1.8           | 6.2           | 0.52     | 3.2            | 10.0    | 5.4      | 3.0       |
|    | OA  | 0.76    | 0.07    | 0.97     | 1.2           | 7.2           | 0.60     | 2.6            | 1.7     | 6.7      | 1.5       |
|    | PA  | 1.16    | 0.17    | 1.21     | 0.29          | 5.6           | 0.24     | 1.7            | 4.7     | 9.8      | 1.0       |
|    | POA | 0.79    | 0.26    | 1.15     | 0.62          | 4.5           | 0.39     | 2.0            | 8.8     | 11.3     | 1.3       |
|    | SA  | 1.19    | 0.12    | 0.87     | 0.48          | 7.8           | 0.43     | 2.6            | 0.6     | 8.0      | 1.1       |
|    | MA  | 0.63    | 0.60    | 1.3      | 0.2           | 2.6           | 0.3      | 0.7            | 7.2     | 7.0      | 1.3       |

EXAMPLE 3

FIG. 1 shows examples of response profiles for FFAu probes used to measure FFAu profiles. The response profile is the fluorescence change as evaluated as (R−Ro)/Ro (ΔR/Ro) for each FFAu added as a complex of the FFA and albumin so that the FFAu concentration is clamped or buffered at 1 nM for every FFAu for which a calibration has been performed. The calculation is performed simply by rearranging equation 2 to solve for ΔR/Ro. The results indicate that none of the probes has absolute specificity for increases the LA fraction of the plasma FFAu to >60%. NA plus coconut oil results in LAU and MA contributing over 90% of the total FFAu (total FFAu=sum of the concentrations of each of the 9 resolved FFAu). NA plus olive oil results in OA as the dominant FFAu but just barely because NA reduces baseline OA to zero and baseline LA is substantially larger than OA. Thus the FFAu profiles that result from NA plus oil are consistent with the conflation of the two effects. The results also show that NA in the absence of infused oil reduces the total FFAu by more than 4 fold (from 9 to 2 nM). Whereas the amount of safflower and coconut oil infused increased the total FFAu to 42 and 92 nM, respectively, consistent with their dominant effects as compared to olive oil (FFAu total=8 nM). These results demonstrate that FFAu profiles can be used to provide a fundamental understanding of the effects of drugs (NA) and can accurately monitor perturbations of the physiologic state. The abbreviations for the individual FFAu are given in Table 1.

EXAMPLE 5

FFAu profiles were determined in rats maintained on low and high fat diets for 6 Months (FIG. 3). Profiles were determined for 4 and 5 animals in each group and the group averages are shown. The analysis was carried out for 9 FFAu however LNA and POA had undetectable levels and are not shown. The sum of the individual FFAu (total FFAu) reveals signficantly larger values for animals on the high fat diet, 22 nM as compared 6 nM for the low fat diet. P values were calculated by a 2 sided t-test for the differences between rats on low fat versus high fat diets for 6 months for each FFAu. Significant differences were observed for AA, DHA and MA. These results demonstrate that a modest physiologic perturbation can be quantitatively monitored by measurement of the FFAu profile. Abbreviations are as in Table 1.

EXAMPLE 6

Effect of diet on mouse FFAu profiles (FIG. 4). Plasma samples from mice fed normal chow, high fat diets and and high fat diets supplemented with fish oil were measured with 20 FFAu probes and the measured R values were analyzed to determine the concentrations of 9 FFAu. The Figure shows the averages and standard errors of the mean (SEM) of the total FFAu (sum of the individual FFAu) and the mole fractions of individual FFAu of N=6 to 9 mice in each group. Also shown are the p values by t-test of the differences between the high and low values in each individual FFAu and for the total FFAu. The results show in most cases a continuous and significant difference from normal to high fat to fish oil supplemented chow. Exceptions are the large DHA fraction, as expected, for fish oil supplemented chow as well as the lack of diet dependence for MA and PA. The increases in AA, are unexpected but might indicate an increased inflammatory response to a high fat diet The continuous increases in SA as well as the decreases in LA and OA may reflect the the high level of SA in the composition of the high fat (lard) diet. In addition there is a striking larger total FFAu for normal as compared to high and fish oil supplemented high fat. This may reflect the larger SA components of high fat and fish oil supplemented high fat diets, because SA binds more tightly to albumin and may therefore displace the weaker binding LA and OA. What is clear is that FFAu profiles reveal striking differences that are mostly unexpected and differ greatly from similar studies measuring total FFA profiles (Buettner et al (2006) J. Mol. Endo 36: 485-501). Moreover there are also striking differences between the rat (FIG. 3) and these mouse results, which might reflect intrinsic species/strain differences or differences in diets.

EXAMPLE 7

TABLE 3

Average FFAu profiles for a nominally healthy population of 18 individuals.
FFAu is total FFAu in nM and individual FFAu are in mole fraction.

|  | FFAu | AA | LNA | LA | OA | PA | POA | SA | DHA | MA |
|---|---|---|---|---|---|---|---|---|---|---|
| Average | 2.7 | 0.033 | 0.010 | 0.278 | 0.239 | 0.146 | 0.000 | 0.021 | 0.013 | 0.260 |

FFAu profiles of human plasma or serum were determined by measuring samples diluted 50 fold in measuring buffer with between 15 and 24 different FFAu probes selected from Table 2. Typical results are shown in Table 3 where FFAu indicates the total FFAu concentration in nM together with the individual mole fractions for the FFAu using the abbreviations of Table 2. In comparison to the rodent profiles (FIGS. 2-4), human profiles reveal substantially larger mole fractions of MA and smaller of LA and in general 2 to 3 fold smaller total FFAu.

TABLE 4

FFAu profiles for human with increasing levels of POA. The amount of POA added increased the mole % of total FFA from 0.6 to 10%. The individual FFAu are in mole fractions.

| Sample | Total FFAu (nM) | AA | LNA | LA | OA | PA | POA | SA | DHA | MA |
|---|---|---|---|---|---|---|---|---|---|---|
| No POA added | 1.41 | 0.077 | 0.000 | 0.217 | 0.200 | 0.105 | 0.000 | 0.097 | 0.002 | 0.301 |
| 0.6% POA added | 1.53 | 0.073 | 0.000 | 0.190 | 0.199 | 0.141 | 0.066 | 0.072 | 0.001 | 0.259 |
| 1.3% POA added | 1.65 | 0.065 | 0.000 | 0.202 | 0.185 | 0.133 | 0.078 | 0.061 | 0.001 | 0.276 |
| 2.5% POA added | 1.90 | 0.053 | 0.000 | 0.183 | 0.155 | 0.178 | 0.157 | 0.051 | 0.002 | 0.222 |
| 5.0% POA added | 2.19 | 0.043 | 0.000 | 0.174 | 0.138 | 0.157 | 0.227 | 0 046 | 0.000 | 0.215 |
| 10% POA added | 2.80 | 0.033 | 0.000 | 0.160 | 0.111 | 0.197 | 0.287 | 0.029 | 0.001 | 0.184 |

Both human and rodent FFAu profiles reveal little or no POA. In contrast, profiles of total FFA report POA levels between 1 and 7%. To ensure that the FFAu probes can quantitate levels of unbound POA, a plasma sample from a mixed population of individual human donors was supplemented with increasing concentrations of POA.

The results shown in Table 4 demonstrate that unbound POA would be determined accurately if total POA were within the range observed in total FFA profiles (1 to 7%).

Moreover they reveal unexpected effects on other components of the FFAu profile. These include a nearly 2-fold increase in PA but decreases in OA, SA, MA and AA with an expected increase in total FFAu.

An additional study reveals the complexity of relating total and unbound profiles. To determine if the low unbound POA levels were due to an interaction with some component of the blood sample matrix an artificial plasma was generated by mixing well defined amounts of the FFA used in Table 4 to fatty acid free human serum albumin in Measuring buffer. The results shown in Table 5 demonstrate the complex interactions that govern the FFAu profile. As expected, the weaker binding to albumin of MA, AA, LA and POA yields larger FFAu mole fractions than their total FFA fractions. However, the dramatic decreases in in the unbound OA and PA relative to their total fractions and the relatively unaffected SA fractions are not easily understood from measurements of the individual albumin binding affinities. Together with the results of Table 4, this suggests a complex interation among the different albumin bound FFA that can substantially alter the FFAu profile. These findings in human blood plasma and FFA complexes with HSA contrasts with Huber et al (2006) 45:14263-14274 who, on the basis of aqueous complexes of 5 FFA with bovine serum albumin, concluded that the measured FFAu profiles were consistent with no interactions among the 5 different FFA.

TABLE 5

FFAu measured in artificial plasma (column 3) produce by mixing the listed FFA in the amounts listed in column 2.

|     | % total FFA | % FFAu |
| --- | --- | --- |
| AA  | 1.4 | 5.8 |
| LA  | 7.4 | 21.1 |
| OA  | 39.2 | 5.6 |
| SA  | 10.8 | 9.3 |
| POA | 7.2 | 16.9 |
| PA  | 31.1 | 8.2 |
| MA  | 3 | 33 |

EXAMPLE 8

Non alcoholic fatty liver disease (NAFLD) is estimated to affect 20% of the world's population. The disease is progressive and in advanced forms results in serious liver injury and is termed NASH. NAFLD begins with the accumulation of triglyceride within the liver, which is thought to be due to elevated levels and possibly altered profiles of plasma FFA, The presence of the disease at all stages is difficult to determine and currently a definitive diagnosis requires a liver biopsy. A simple non-invasive test for the presence and stage of the disease would help greatly in its management. We have determined FFAu levels and profiles in healthy controls and patients with NAFLD/NASH. In panel A) of FIG. 5 results of FFAu profiles measured in biopsy confirmed patients with non alcoholic fatty liver disease (NAFLD/NASH) are compared with controls (healthy donors whose NAFLU status was unknown). A t-test was used to evaluate differences in the individual FFAu fractions. Results from a separate study are shown in panel B) where FFAu profiles are compared in biopsy confirmed patients with mild NASH and biopsy confirmed controls. In all cases red top serum tubes were used for sample collection and measurements were performed with 20 FFAu probes. The results of both studies reveal highly significant differences for MA, PA and SA in which MA and SA mole fractions are smaller and PA is larger in patients versus controls. In both studies no significant difference was observed for LA or DHA. Moreover, although the patient-control differences did not reach significance in the study of B) the pattern for POA, OA, LNA and AA was the same as for A) where, presumably because of the larger number of participants the differences were significant. The sum of 9 FFAu in nM was larger for the patients than controls in both studies but did not reach significance. Total FFA profiles in similar patient-controls have failed to observe differences as in FIG. 5.

EXAMPLE 9

Unbound and total FFA profiles are compared for humans and rodents in FIG. 6. For humans the total FFA profiles are averages of the 9 FFA (normalized to 100%) for control populations of the 7 studies cited in [0040]. The FFAu profiles are those for the controls in FIG. 5A. For rodents the total FFA profiles are for rats on standard chow (also normalized to 100%) from the study of (Buettner et al (2006) J. Mol Endo 36: 485-501), The FFAu profiles are those from FIG. 4 for mice on normal chow. For most FFA the differences between total and FFAu are in the same direction for human and rodent. However these differences are substantially larger for humans, most dramatically for MA, AA, LA, OA and PA. The total FFAu differences are of lesser magnitude for rodents although MA and POA reveal large differences. These results emphasize the complexity of factors that govern the physiologically relevant, FFAu profile.

EXAMPLE 10

FFAu probes were used for rapid screening of algae species GA0214, GA0216, GA0223 and GA0224 to identify species and growth conditions that would maximize the production of the omega-3 FFA, especially EPA. Conventional methods such as GC-MS or LC-MS require extensive sample preparation, substantial amounts of sample and a substantial amount of time to run and analyze a sample. Typically, even with automated systems analysis of a sample requires several hours, so that fewer than 10 samples can be analyzed per 24 hour day. In contrast, using FFAu probes several thousand samples can be analyzed per day, requiring only modest sample preparation and typically sample volumes <50 μL.

In this example, 4 strains of algae were screened to determine whether FFAu probes could accurately quantitate levels of free EPA produced from algae. From conventional analysis it was known that GA0214 and GA0216 produce undetectable EPA whereas GA0223 and GA0224 produced substantial amounts of EPA but no DHA. Two FFAu probes were used for this screen: L127 which has a high degree of specificity for DHA and EPA and L61 which is not specific for DHA or EPA. Approximately 20 μL samples of the algae cultures, after brief sonication, were diluted about 10 fold in measuring buffer in which HEPES was 100 mM and the FFAu probes were added to give a concentration of 0.25 μM in the wells of a 96 well micro-titer plate. The 96 well plate, with multiple replicates of the samples, was screened by measuring the fluorescence intensities at 457 and 550 nm, in each well in a total measurement time of 60 seconds for the plate. The results were analyzed to determine (R−Ro)/(Rm−R) which is proportional to the total FFAu concentration. As is apparent in Table 6, the L127 which is specific for EPA (20 carbons) and DHA (22 carbons) shows almost no response to the no EPA samples but

TABLE 6

Screening Algae species for production of EPA with FFAu probes specific (L127) and non-specific (L61) for EPA.

| Probe | (R-Ro)/(Rm-R) | | | | Average EPA/ No EPA |
|---|---|---|---|---|---|
| | No EPA | | EPA | | |
| | GA0214 | GA0216 | GA0223 | GA0224 | |
| L127 (20, 22) | 0.02 | 0.01 | 1.17 | 0.51 | 71.1 |
| L61 (16, 18) | 0.52 | 0.62 | 3.22 | 1.69 | 4.3 | approximately 70 fold larger response to the EPA producing species. The L61 response indicates that both types of cells produce FFAu (mostly 16 and 18 carbons) but the EPA produce more FFA overall so that the ratio for the non-EPA FFAu is about 4.

These results demonstrate that screening for specific FFAu and even complete FFAu profiles can be performed with orders of magnitude smaller sample sizes, obtained without organic extraction, and in times that are orders of magnitude faster than any other method.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for identifying and measuring an amount of one or more unbound free fatty acids (FFAu) in a biological sample comprising the steps of:
   (a) providing a set of probes comprising a plurality of FFAu probes wherein each probe in the plurality of FFAu probes has a specificity for a plurality of FFAu of interest that is different from and complementary to the specificity of one or more other probes in the set of probes, and wherein at least 60% of probes in the set of probes is labeled at a cysteine residue;
   (b) combining each individual probe from the plurality of FFAu probes with a separate aliquot of the biological sample for each individual probe;
   (c) measuring a fluorescence index at two different emission wavelengths for each probe in the combined probe and aliquot of the biological sample from step (b);
   (d) calculating the ratio of the fluorescence index at the two wavelengths from step (c) for each probe; and
   (e) determining an identity and measuring an amount of the one or more FFAu present in the biological sample based on the calculated ratio of fluorescence index for each probe,
   wherein the set of probes comprises more probes than the number of FFAu to be identified and measured.

2. The method of claim 1, wherein the plurality of FFAu probes from the set of probes is selected from TABLE 2.

3. The method of claim 1, wherein the accuracy of the calibration of the probes is assessed by requiring the total FFAu ($FFA_u^T$) to be equal for each probe using equation (4) for each probe's $FFA_u^T$ $$FFA_u^T = \frac{R^j - R_o^j}{\left(\left\langle \frac{Rm^j}{Q^j Kd^j}\right\rangle - R^j \left\langle \frac{1}{Q^j Kd^j}\right\rangle\right)}, \quad (4)$$

for each probe j, wherein $R^j$ is the blank subtracted fluorescence intensity at wavelength 1 divided by the blank subtracted fluorescence intensity at wavelength 2 in the presence of each FFAu from 1 to N, wherein N is the total number of FFAu;
wherein $R_o^j$ is the blank subtracted fluorescence intensity at wavelength 1 divided by the blank subtracted fluorescence intensity at wavelength 2 in the absence of each FFAu for each probe;
wherein $R_m^j$ is the R value at saturation;
wherein $Q^j$ is the is the ratio of the fluorescence intensity at wavelength 2 with no FFAu to the fluorescence intensity at wavelength 2 at saturation;
wherein $K_d^j$ is the equilibrium dissociation constant for probe j and each FFAu;
wherein the brackets < > represent $\alpha_i$ weighted averages for the indicated quantities, and wherein where the sum of $\alpha_i=1$;
wherein the $FFA_u^T$ values are calculated for each probe and the average value and standard deviation is calculated for the first set of probes used to determine the identity and amount of FFAu present in the biological sample and wherein probes whose FFAu deviate significantly from the average are recalibrated and the FFAu analysis is repeated and wherein the FFAu total should be the same value for each probe.

4. The method of claim 1, further comprising using the identity and amount of FFAu to diagnose disease in humans or animals.

5. The method of claim 1, further comprising using the identity and amount of FFAu to monitor disease progression in humans or animals.

6. The method of claim 1, further comprising using the identity and amount of FFAu to determine the risk of future disease in humans or animals.

7. The method of claim 1, further comprising using the identity and amount of FFAu to monitor effects of drugs in humans or animals.

8. The method of claim 1, further comprising using the identity and amount of FFAu to monitor effects of diet in humans or animals.

9. The method of claim 1, further comprising using the identity and amount of FFAu to determine the role of specific FFAu in cellular and biochemical pathways.

10. The method of claim 1, further comprising using the identity and amount of FFAu to screen cells and microorganisms for alterations in fatty acid pathways.

11. The method of claim 10, wherein alteration of fatty acid pathways comprises the production of specific oils.

12. The method of claim 1, further comprising using the identity and amount of FFAu to optimize enzymatic processes.

13. The method of claim 1, wherein the fluorescence index is intensity, polarization and/or lifetime of the probe, in the presence and absence of each FFAu in a set of FFAus of interest.

14. The method of claim 1, wherein the identity and amount of at least nine distinct FFAu are determined.

15. The method of claim 1, wherein each probe is labeled at lysine 27 or at a cysteine.

16. The method of claim 1, wherein the plurality of FFAu probes are provided on a surface.

17. The method of claim 16, wherein the surface is a cuvette, a cartridge, a strip, or a multi-well plate.

18. The method of claim 1, wherein the biological sample comprises whole blood, blood plasma, blood serum, urine, cerebral spinal fluid, saliva, gastric juices, interstitial fluid, lymph, cell extract, or cell medium.

19. The method of claim 1, wherein the one or more FFAu that is identified and measured comprises myristate (MA), linolenate (LNA), palmitoleate (POA), arachidonate (AA), docosahexaenoate (DHA), linoleate (LA), oleate (OA), palmitate (PA), laurate (LAU), eicosapentaenoate (EPA), vaccenate (VA), and stearate (SA).

* * * * *

UNITED STATES PATENT AND TRADEMARK OFFICE
CERTIFICATE OF CORRECTION

PATENT NO. : 10,705,101 B2
APPLICATION NO. : 15/037910
DATED : July 7, 2020
INVENTOR(S) : Kleinfeld et al.

Page 1 of 3

It is certified that error appears in the above-identified patent and that said Letters Patent is hereby corrected as shown below:

On the Title Page

In Column 2, item (56), Other Publications, Line 2, delete "Dectection" and insert -- Detection --.

In the Drawings

In sheet 2 of 6, FIG. 2, Line 6 (approx.), delete "Nicotnic" and insert -- Nicotinic --.

In sheet 4 of 6, FIG. 4, Line 14 (approx.), delete "ttests" and insert -- t-tests --.

In sheet 5 of 6, FIG. 5, Line 1, delete "(ttests)" and insert -- (t-tests) --.

In sheet 5 of 6, FIG. 5, Line 15 (approx.), delete "ttests" and insert -- t-tests --.

In the Specification

In Column 1, Line 18, delete "TXT."" and insert -- TXT," --.

In Column 1, Line 42, delete "(for" and insert -- for --.

In Column 1, Line 61, delete "(Richieri" and insert -- Richieri --.

In Column 2, Line 27, delete "eiconsanoids," and insert -- eicosanoids, --.

In Column 3, Line 25, delete "Rj" and insert -- $R^j$ --.

In Column 3, Line 31, delete "probe:" and insert -- probe; --.

In Column 3, Line 32, delete "is the is the" and insert -- is the --.

Signed and Sealed this
Sixth Day of October, 2020

Andrei Iancu
*Director of the United States Patent and Trademark Office*

CERTIFICATE OF CORRECTION (continued)
U.S. Pat. No. 10,705,101 B2

In Column 3, Line 46, delete "re" and insert -- are --.

In Column 4, Line 24, delete "profit s" and insert -- profiles --.

In Column 4, Line 41, delete "acid" and insert -- and --.

In Column 4, Line 67, delete "Bemlohr" and insert -- Bernlohr --.

In Column 6, Line 9, delete "slate." and insert -- state. --.

In Column 7, Line 19, delete "hound" and insert -- bound --.

In Column 7, Line 31, delete "(KA)" and insert -- (Kd) --.

In Column 8, Line 59, delete "determing" and insert -- determining --.

In Column 8, Line 67, delete "FFAu." and insert -- FFAu, --.

In Column 11, Line 7, delete "the" and insert -- is the --.

In Column 11, Line 23, delete "mult-well" and insert -- multi-well --.

In Column 12, Line 34, delete "ADTFAB2." and insert -- ADIFAB2. --.

In Column 13, Line 13 (approx.), delete "the" and insert -- with the --.

In Column 13, Lines 17-18 (approx.), delete "wave length" and insert -- wavelength --.

In Column 13, Line 21, delete "monochromater," and insert -- monochromator, --.

In Column 13, Line 22, delete "monochromaters" and insert -- monochromators --.

In Column 14, Line 54, delete "indentified" and insert -- identified --.

In Column 16, Line 8, delete "affininity" and insert -- affinity --.

In Column 19, Line 17 (approx.), delete "signficantly" and insert -- significantly --.

In Column 19, Line 39, delete "and and" and insert -- and --.

In Column 20, Line 5 (approx.), delete "the the" and insert -- the --.

In Column 21, Line 20 (approx.), delete "interation" and insert -- interaction --.

In Column 21, Line 45, delete "Non alcoholic" and insert -- Non-alcoholic --.

CERTIFICATE OF CORRECTION (continued)
U.S. Pat. No. 10,705,101 B2

In Column 21, Line 50, delete "FFA," and insert -- FFA. --.

In Column 21, Line 58 (approx.), delete "non alcoholic" and insert -- non-alcoholic --.

In Column 21, Line 60, delete "NAFLU" and insert -- NAFLD --.

In Column 22, Line 22, delete "501)," and insert -- 501). --.

In Column 22, Line 59, delete "micro-titer" and insert -- microtiter --.

In the Claims

In Column 25, Line 49 (approx.), Claim 3, delete "is the is the" and insert -- is the --.

In Column 25, Line 56 (approx.), Claim 3, delete "wherein where" and insert -- wherein --.

SEQUENCE LISTING

<160> NUMBER OF SEQ ID NOS: 1

<210> SEQ ID NO 1
<211> LENGTH: 139
<212> TYPE: PRT
<213> ORGANISM: Rattus norvegicus
<220> FEATURE:
<221> NAME/KEY: MUTAGEN
<222> LOCATION: (131)...(131)
<223> OTHER INFORMATION: rat intestinal fatty acid binding protein with
      Glu 131 to Asp substitution
<220> FEATURE:
<221> NAME/KEY: VARIANT
<222> LOCATION: (131)...(131)
<223> OTHER INFORMATION: COOH-terminal affinity tag comprising Arg 132,
      Gly 133 and 6 histidines

<400> SEQUENCE: 1

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Leu Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Asp Arg Gly His His His His His His
    130                 135